(12) United States Patent
Dickinson et al.

(10) Patent No.: US 6,737,044 B1
(45) Date of Patent: May 18, 2004

(54) AEROSOL COMPOSITION

(75) Inventors: Paul Alfred Dickinson, Cardiff (GB); Simon John Warren, Heath Cardiff (GB)

(73) Assignees: University College Cardiff Consultants Limited, Cardiff (GB); Cardiff Scintigraphics Limited, Cardiff (GB)

(*) Notice: Subject to any disclaimer, the term of this patent is extended or adjusted under 35 U.S.C. 154(b) by 0 days.

(21) Appl. No.: 09/647,331

(22) PCT Filed: Apr. 1, 1999

(86) PCT No.: PCT/GB99/01019

§ 371 (c)(1),
(2), (4) Date: Jan. 30, 2001

(87) PCT Pub. No.: WO99/51205

PCT Pub. Date: Oct. 14, 1999

(30) Foreign Application Priority Data

Apr. 3, 1998 (GB) .............................. 9807232

(51) Int. Cl.⁷ ............................ A61K 9/14; A61K 9/00; B05B 9/04; A61M 11/00
(52) U.S. Cl. ................... 424/46; 424/489; 128/200.14; 128/200.23; 514/2; 514/826; 514/951
(58) Field of Search .............. 424/46, 489; 128/200.14, 128/200.23; 514/2, 826, 951

(56) References Cited

U.S. PATENT DOCUMENTS

| | | | |
|---|---|---|---|
| 5,626,871 A | * | 5/1997 | Makino et al. ............. 424/451 |
| 5,955,439 A | | 9/1999 | Green ......................... 541/23 |

FOREIGN PATENT DOCUMENTS

| | | |
|---|---|---|
| CA | 2062854 | 9/1992 |
| EP | 054112 A2 | 9/1992 |
| EP | 0372777 B1 | 1/1993 |
| EP | 0561166 A1 | 9/1993 |
| EP | 0804946 A1 | 11/1997 |
| GB | WO-95/24889 A1 * | 9/1995 |
| GB | WO-96/19968 A1 * | 7/1996 |
| WO | WO 87/07502 | 12/1987 |
| WO | WO 91/1117 | 8/1991 |
| WO | WO 92/00061 | 1/1992 |
| WO | WO 92/06675 | 4/1992 |
| WO | WO 92/08447 | 5/1992 |
| WO | WO 95/24889 | 9/1995 |
| WO | WO 96/19968 | 7/1996 |
| WO | WO 99/51205 | 10/1999 |

OTHER PUBLICATIONS

Bower et al., Fractal morphology of drug aggregates in aersol propellant suspensions, *International Journal of Pharmaceutics*, vol. 118, 1995, pp. 229–235.

* cited by examiner

*Primary Examiner*—Frederick Krass
*Assistant Examiner*—Clinton Troy Ostrup
(74) *Attorney, Agent, or Firm*—Woodcock Washburn LLP

(57) ABSTRACT

An aerosol composition comprising a propellant and a first particulate material comprising particle having a median aerodynamic diameter within the range 0.05 to 11 μm, such as a medicament suitable for pulmonary inhalation, and a second particulate material comprising particles having a median volume diameter within the range 15 to 200 μm. The presence of the second particulate material provides good suspension properties, particularly where the propellant is a hydrofluoro alkane.

51 Claims, 3 Drawing Sheets

AEROSOL COMPOSITION

Figure 1:
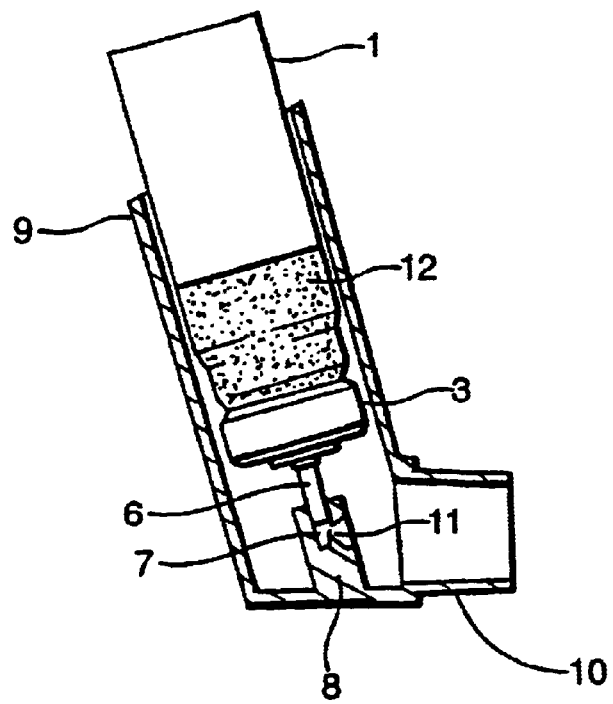

The present invention relates to an aerosol composition. In particular the present invention relates to an aerosol composition in the form of a suspension comprising liquid propellant and particulate material.

Effective use of an aerosol composition in the form of a suspension usually requires the suspension to comprise a uniform dispersion of particulate matter in order to ensure the production of an aerosol of known components in known amounts. Inhomogeneous dispersions can occur due to poor dispersibility of the particulate matter in the propellant and/or a tendency of the particulate matter to aggregate and possibly even to aggregate irreversibly.

Aerosol compositions comprising particulate matter in the form of a suspension can be used for the delivery of a number of active agents. A particular application comprises pharmaceutical suspensions for administration of a drug in particulate form.

An example of a pharmaceutical application of a particulate-containing aerosol composition is inhaler suspensions. Inhaler suspensions are used for delivery of a particulate medicament to the lungs or upper airway passages. Suitably the suspension is contained in a container fitted with a metering valve. A known dose can thus be administered on each occasion of use. Such containers can be convenient to use and are readily portable.

Such a metered dose inhaler conventionally consists of a pressurised container which has a metering valve of fixed volume to measure individual doses of a suspension of medicament held in the container. In order to ensure the administration of an accurate dose of suspended particulate medicament it is essential that the suspension is consistently and homogeneously dispersed and the valve performance is reproducible and effective throughout the life of the container. The suspension conventionally comprises medicament particles dispersed in a liquefied gas which in use acts as a propellant. On depressing the valve stem of the metering valve the propellant fraction of the metered dose rapidly vaporises so as to aerosolise the suspended particulate medicament which is then inhaled by the user.

Traditionally, chlorofluorocarbons such as CFC-11, CFC-12 and CFC-114 have been employed as propellants in metered dose inhalers. A particulate medicament intended for pulmonary administration needs to have a particle size with a median aerodynamic diameter between about 0.05 $\mu$m and about 11 $\mu$m. This range of size of medicament particle is important in inhalers. Larger particles will not necessarily or readily penetrate into the lungs and smaller sized particles are readily breathed out. However, particles between about 0.05 $\mu$m and about 11 $\mu$m can possess a high surface energy and can therefore be difficult to disperse initially in the propellant, and once dispersed can exhibit a tendency to aggregate undesirably and rapidly, leading eventually to irreversible aggregation of the particles. In the case of CFC as a propellant this problem was overcome by the addition of a surfactant soluble in the CFC which coats the medicament particles and prevents aggregation by steric hindrance. The presence of surfactant is also believed to be an aid to valve performance. In practice medicament particles were homogenised in the liquid CFC-11 with the inclusion of a propellant soluble surfactant such as lecithin, oleic acid or sorbitan trioleate. The resulting bulk suspension was dispensed into individual metered dose inhalers and a high vapour pressure propellant such as liquefied gas CFC-12/CFC-114 added. Such arrangements proved satisfactory in use, although the added surfactant could adversely affect the perceived taste of the inhaler in use. For example oleic acid could impart a bitter taste.

In recent years the detrimental effect of chlorofluorocarbons on the ozone layer in the earth's stratosphere has become apparent. The continued use of CFC has therefore become unacceptable and in some instances has been banned by local regulations.

Alternative propellants which share some similar physical properties to those of previously used CFC propellants and which have been suggested for use in metered dose inhalers are hydrofluoroalkanes, notably HFA-134a and HFA-227. Problems however exist on attempting to formulate the hydrofluoroalkanes into an aerosol composition such as an inhaler suspension. Firstly, the acceptable surfactants employed in CFC based suspensions are not sufficiently soluble in hydrofluoroalkanes to prevent irreversible aggregation of the particulate medicament occurring. Secondly, neither HFA-134a nor HFA-227 is a liquid at an acceptable temperature so that bulk homogenisation with particulate material prior to filling into individual pressured containers is only possible if carried out under pressure.

A number of proposals have been made in an attempt to employ hydrofluoroalkanes as the propellant in pressurised metered dose inhalers for example a patent specification (WO 92/06675) in the name of Minnesota Mining and Manufacturing Company suggests the use of non-volatile co-solvents to modify the solvent characteristics of the hydrofluoroalkane propellant and thereby increase the solubility and hence permit the use of the surfactants traditionally employed in CFC based metered dose inhalers. The presence of the co-solvent however may result in less desirable aerosol properties. Moreover the alcohol nonvolatile co-solvents suggested can impart an unpleasant sharp taste.

Patent specifications (WO 91/11173 and WO 92/00061) in the name of Fisons suggest the use of alternative surfactants which are sufficiently soluble in HFA-134a and HFA-227. The surfactants proposed however may present toxicity problems in use. Extensive and expensive toxicity studies are therefore required before the pharmaceutical regulatory authorities will permit their inclusion in a product intended for human use.

Glaxo Group Limited in WO 96/19968 suggests a pharmaceutical aerosol formulation which comprises particulate medicament, at lease one sugar and a fluorocarbon or hydrogen containing chlorofluorocarbon propellant. The particle size of the sugars used in the formulations are said to be selected using conventional techniques such as milling or micronisation. The suspension stability of the aerosol formulations is said to be particularly impressive.

Other proposals to provide a metered dosed inhaler employing hydrofluoroalkane are found in patent specification no. WO 92/08477 in the name of Glaxo Group Limited and patent specification no. EP 372777 in the name of Riker Laboratories, Inc.

A need therefore exists to provide an aerosol composition suitable for use in for example, an inhaler, comprising a suspension of particulate matter in a propellant, which composition has good dispersion characteristics, a reduced tendency to aggregate and can in use be effectively aerosolised with good valve performance.

It is an object of the present invention to provide an aerosol composition including a particulate material suitable for use in for example an inhaler which composition exhibits both a reduced tendency for the particulate material to aggregate undesirably and ready and homogeneous dispersion of the particulate material, and permits acceptable delivery of the particulate material.

It is a further object of the present invention to provide an additive comprising a particulate material for use in the preparation of such an aerosol composition.

It is a further object of the present invention to provide a container, such as an inhaler, containing such a composition.

It is a further object of the present invention to provide a container, such as metered dose inhaler incorporating a valve dispensing mechanism, containing such a composition, the composition ensuring both good suspension properties and good valve performance over the life of the container.

Further objects of the present invention include a method of preparing a container containing such a composition and a method of administering the composition.

According to a first aspect of the present invention there is provided an aerosol composition comprising a propellant and contained therein a first particulate material comprising particles having a median aerodynamic diameter within the range 0.05 to 11 $\mu$m and a second particulate material comprising particles having a median volume diameter within the range 15 to 200 $\mu$m.

The propellant is in liquid form during storage of the composition and evaporates in use. The inclusion of a second particulate material having a median volume diameter in the range 15 to 200 $\mu$m in combination with the first particulate material having a median aerodynamic diameter in the range 0.05 to 11 $\mu$m has unexpectedly been found to enhance dispersion and to reduce particulate aggregation, leading to a reduced risk of irreversible aggregation, whilst still permitting good aerosol performance of the suspension in use. The result is unexpected as prima facie the inclusion of extra insoluble solids had been considered to be inappropriate leading to less desirable aerosol characteristics and poor valve performance due for example to blocking. The present invention can thus permit the delivery of particulate material at a known and consistent concentration.

Although we do not wish to be bound by any theory we believe that the presence of the second particulate material having a median volume diameter in the range 15 to 200 $\mu$m reduces the risk of irreversible aggregation of the first particulate material as the larger particles are unable to pack sufficiently close together to permit packing of particles in the primary energy minimum. By "irreversible aggregation" we mean aggregation of particles which cannot be dispersed by hand held shaking.

Within the aerosol composition the first and second particulate materials are believed to be present as either a simple admixture or with some or all of the smaller first particulate material particles interacting with the larger particles of the second particulate material. The presence of the second particulate material can thus help to prevent non-specific adsorption of the first particulate material to the inside surface of a container containing the aerosol composition and to break up any aggregates of the first particulate material that may form.

The presence of the second particulate material in the propellant can lead to flocculation i.e. loose association of the suspended particles into a fluffy floc. Flocculation differs from irreversible aggregation in that it occurs in the secondary energy minimum and is dispersible by hand held shaking. Flocculation of the second particulate material can occur in the propellant either in the absence or in the presence of the first particulate material. Where flocculation occurs in the absence of the first particulate material, the equivalent composition containing additionally the first particulate material can surprisingly inhibit the flocculation occurring. Where flocculation of the second particulate material does however occur in the propellant in the presence of the first particulate material it is not detrimental to the present invention as it can be removed by hand held shaking prior to use of the aerosol. It may moreover even be beneficial in preventing irreversible aggregation in the primary energy minimum.

By "volume diameter" is meant the diameter of a sphere having the same volume as the particle. The second particulate material is selected according to its volume diameter as it is the physical bulk of the second particulate material which is believed to be important in determining the properties of the suspension.

By "aerodynamic diameter" is meant the volume diameter multiplied by the square root of the ratio of the particle density (g cm$^{-3}$) to the density of a particle with same volume diameter having a density of 1 g cm$^{-1}$. The first particulate material is thus selected according to its volume diameter having the stated consideration for its density. In the definition of "aerodynamic diameter" given above the assumption is made, in keeping with conventional aerosol practice, that the first particulate material can be deemed to be spherical in shape. Moreover, where as is usually the case, the first particulate material has a particle density between about 1 and 2 g cm$^{-3}$ the aerodynamic diameter of the first particulate material is approximately equivalent to its volume diameter According to another aspect of the present invention there is provided a container containing the aerosol composition according to the present invention, the container including a valve outlet. Suitably the contents of the container are pressurised up to a pressure of 6.893×10$^5$Pa (100 psig). Preferably the container includes a metered valve outlet capable of delivering a measured dose of suspension in the form of an aerosol. Preferably the container is in the form of an inhaler. According to another aspect of the present invention there is provided an inhalation device incorporating the said container.

According to another aspect of the present invention there is provided a method for preparing an aerosol composition comprising:

(a) forming a mixture of a first particulate material comprising particles having a median aerodynamic diameter within the range 0.05 to 11 $\mu$m and a second particulate material having a median volume diameter within the range 15 to 200 $\mu$m;

(b) dispensing measured portions of respectively said mixture and a propellant into a container, and (c) sealing the container.

Alternatively all of the ingredients can be admixed prior to dispensing into individual containers.

Suitably the container is pressurised and includes an outlet valve, preferably a metered dose dispensing valve.

The mixture of the first particulate material and the second particulate material permits ready dosing of the mixture into the container due to improved flow characteristics compared to the first particulate material in the absence of the second particulate material. Suitably the mixture is dosed into the container before the propellant. The enhanced dispersion characteristics of the mixture in the added propellant permits the omission of the step of providing a homogeneous suspension prior to dispensing into a container. In keeping with conventional procedures for preparing an aerosol the container can be sealed following the dosing of the mixture into the container, with the propellant being subsequently dosed into the container through for example an outlet valve forming a part of a seal.

According to another aspect of the present invention there is provided a mixture of a first particulate material having a median aerodynamic diameter within the range 0.05 to 11 μm and a second particulate material having a median volume diameter within the range 15 to 200 μm.

According to another aspect of the present invention there is provided a use of a particulate material, for example lactose, having a median volume diameter lying in the range 15 to 200 μm to enhance the dispersion characteristics of a particulate material having a median aerodynamic diameter lying in the range 0.05 to 11 μm in suspension in a propellant.

According to another aspect of the present invention there is provided a method of administering a particulate material to a patient in need thereof comprising the patient inhaling an aerosol comprising vaporised propellant and a mixture of an active agent comprising particles having a median aerodynamic diameter lying in the range 0.05 to 11 μm and a second particulate material comprising particles having a median volume diameter lying in the range 15 to 200 μm. In applying the method, forces generated by vaporisation of the propellant separate particulate active agent from the mixture such that the active agent is available and suitable for lung deposition after inhalation. The method can be applied orally or nasally.

According to another aspect of the present invention there is provided an aerosol composition comprising a mixture of an active agent comprising particles having a median aerodynamic diameter lying in the range 0.05 to 11 μm and a second particulate material comprising particles having a median volume diameter lying in the range of 15 to 200 μm for use in the treatment of respiratory diseases.

Preferably the first particulate material has a median aerodynamic diameter within the range 1 to 10 μm, more preferably within the range 1 to 5 μm. Where the present aerosol composition is employed as an inhaler such preferred ranges are optimum for respiratory delivery.

Preferably the second particulate material has a median volume diameter of more than 20 μm suitably within the range 20 to 125 μm, more preferably within the range 25 to 125 μm, even more preferably within the range 30 to 125 μm, even more preferably still within the range 38 to 125 μm. Preferred ranges may moreover include 45 to 125 μm and 63 to 125 μm.

Suitably the second particulate material is sufficiently soft to ensure that no or minimal damage, for example, such as scratching is sustained by the valve over the lifetime of, for example, a metered dose inhaler. A metered dose inhaler may have the potential to provide in excess of one hundred shots or actuations and ideally needs to be reproducible at a pattern of usage of two shots four times daily. Absence of any significant damage to the valve is essential to ensure that over the lifetime of the container a sufficiently consistent shot or actuation of each dose of homogeneous suspension is provided to ensure appropriate and sufficiently accurate delivery of, for example, medicament as the first particulate material.

A sufficiently soft second particulate material would also reduce the likelihood of valve leakage potentially attributable to particulate material lodging in the valve head and preventing proper reseating of the valve after each use. Preferable the softness of the second particulate material is less than 6.5 Mohs hardness, more preferably less than 5 Mohs hardness, even more preferably less than 4 Mohs hardness and even more preferably less than 3 Mohs hardness. The minimum Mohs hardness is 0. The preferred range is between 2 to 4, the more preferred range is 2 to 3 Mohs hardness.

Performance of the valve in a pressurised container containing the present composition may additionally and/or alternatively be adversely affected by the shape of the particle comprising the second particulate material. Preferably the second particulate material is substantially spheroidal or ellipsoidal. Although we do not wish to bound by any theory, it is postulated that a second particulate material having a generally curved outline will ensure better valve performance due to a reduce likelihood of, for example, scratching of the valve head leading to, possibly, valve leakage and/or inaccurate valve metering. The optimum combination of shape and softness of any second particulate material will, however, be dependent on the material in question and the valve head employed. For example, especially soft second particulate material may yield the necessary good suspension and dispersion properties in the aerosol composition contained in the container prior to use, and yet give no or minimal value damage, even through the particles in the second particulate material are substantially non-spherodial or non-ellipsoidal, for example are in the shape of plates or discs.

The Carr Index is a measure of flow properties of a material in powder form and is substantially dependent on the shape and size of the particles comprising the powder. The Carr Index is defined as:

$$\frac{\text{tapped density} - \text{poured density}}{\text{tapped density}} \times 100\%$$

The Carr Index is measured at 25° C. and compares the density of a powder material when poured into a container with the density of the same material in the same container after the container has been tapped and the powder material has settled to a substantially plateau value.

Preferably the Carr Index for particles comprising the second particulate material and having a population predominantly (i.e. >50%) more than 100 μm in diameter is less than 14%, more preferably less than 12%, even more preferably less than 10%.

Preferably the Carr Index for particles comprising the second particulate material and having a population predominantly (i.e. >50%) less than 100 μm in diameter is less than 28%, more preferably less than 26%, even more preferably less than 24%.

Preferably the Carr Index for particles comprising the second particulate material and having a population predominantly (i.e. >50%) less than 40 μm in diameter is less than 35%, more preferably less than 33%, even more preferably less than 31%.

Preferably the Carr Index for particles comprising the second particulate material and having a population predominantly (i.e. >50%) less than 20 μm in diameter is less than 65%, more preferably less than 63%, even more preferably less than 61%.

Preferably the weight ratio of the first particulate material to the second particulate material lies in the range 1:0.1 to 1:500, the weight being that of the first particulate material and the weight of the second particulate material admixed with the propellant and thus includes any material dissolved in the propellant. More preferably the weight ratio of the first particulate material to the second particulate material lies in the range 1:1 to 1:200, even more preferably within the range 1:10 to 1:100, even more preferably within the range of 1:25 to 1:67. The actual ratio selected for any particular suspension will depend inter alia on the solubility of each of the first and second particulate materials in the propellant, the dosage or usage requirements of the particulate materials and the extent of any interaction between the first particulate material and the second particulate material. An alternative preferred range of the weight ratio of first to second particulate material is 1:5 to 1:50.

The actual amount and size of each particulate material used will depend inter alia on the solubility of each particulate material in the propellant and the type and dose of each particulate material required. Suitably however the aerosol composition comprises 80 to 99.999 wt % propellant, more suitably 90 to 99.9 wt % propellant. The total weight of particulate material employed, measured as including dissolved and undissolved material, is thus suitably 20 to 0.001 wt % with respect to the total weight of the composition, more preferably 10 to 0.1 wt % with respect to the total weight of the composition. The concentration of the first particulate material in the composition, including dissolved and undissolved material, preferably lies in the range 1 to 0.0001 wt %, more preferably in the range 0.5 to 0.005 wt % with respect to the total weight of the composition.

Each of the first and second particulate materials may be partially soluble in the propellant. Preferably the solubility of the first particulate material in the propellant does not exceed 49.9 wt % with respect to the total weight of the substance comprising the first particulate material present. More preferably the solubility of the first particulate material in the propellant does not exceed 10 wt %, even more preferably 1.0 wt % with respect to the total weight of first particulate material present.

Preferably the solubility of the second particulate material in the propellant does not exceed 49.9 wt % with respect to the total weight of the substance comprising the second particulate material present. More preferably the solubility of the second particulate material does not exceed 10 wt %, even more preferably 1.0 wt % with respect to the total weight of the second particulate material present. Low solubility of each of the first particulate material and the second particulate material is preferred in order to avoid stability problems such as the risk of particle growth due to Ostwald ripening.

Preferably the ratio of the density of the second particulate material to the density of the propellant lies in the range 0.6:1 to 1:1.6. Too large a density difference between the density of the second particulate material and the density of the propellant is preferably avoided. The optimal density difference can be ascertained in each instance, particularly having regard to the ambient temperature effecting the density of the propellant and any tendency of the second particulate material to flocculate in the presence of the first particulate material. When not equal to the density of the propellant the density of the first particulate material and the density of the second particulate material are in some instances suitably both either more than or less than the density of the propellant. Should the first and second particulate materials exhibit any tendency to sediment or cream (i.e. float) their uniform dispersion in the propellant can thus be more readily achieved.

The substance comprising the second particulate material is suitably chemically unreactive with respect to the first particulate material. The present aerosol composition can be in the form of a pharmaceutical composition. Where the first particulate material is a medicament, the second particulate material preferably does not modify the biopharmaceutical profile of the medicament comprising the rust particulate material. The second particulate material can comprise one or more active or inactive agents or a mixture thereof, for example it can comprise one or more pharmacologically inert substances, one or more pharmacologically active substances, one or more flavour imparting substances or a mixture thereof. Where the present aerosol composition is intended for use as an inhaler, the second particulate material can for example comprise a pharmacologically active substance for oral administration.

Where the first particulate material is a medicament, the second particulate material should be acceptable for administration to a human. Preferably it will be a substance which already possesses regulatory approval and has a desirable safety profile. For example where the present aerosol composition is intended for use as an inhaler the second particulate material may already possess regulatory approval for use in pulmonary administration. The second particulate material selected should preferably be relatively inexpensive and readily available.

Suitable substances for use as the second particulate material in at least an inhaler may be selected from carbohydrates such as sugars, mono-, di-, tri-, oligo- and polysaccharides and their reduced forms such as sorbitol; from amino acids, di-, tri-, oligo- and poly-peptides and proteins; and from physiologically acceptable derivatives, forms, salts and solvates thereof; and from mixtures thereof. Preferably the second particulate material is selected from lactose, glucose and leucine and mixtures thereof. The material can be in any appropriate form, for example lactose can be α-lactose, β-lactose, anhdrous lactose, amorphous or any form of lactose or any mixture thereof. Leucine and spray dried lactose are especially preferred where valve performance may be of importance as they are each relatively soft. Spray dried lactose additionally is substantially spheroidal and may be preferred where valve performance is of importance.

Where the first particulate material is a particulate medicament suitable for oral or nasal inhalation and the aerosol composition is intended for use as an inhaler, examples of suitable particulate medicaments for use in the treatment and prevention of asthma and other conditions associated with reversible airways obstruction include either alone or in any combination:

(i) salbutamol, salbutamol sulphate, mixtures thereof and physiologically acceptable salts and solvates thereof, (ii) terbutaline, terbutaline sulphate, mixtures thereof and physiologically acceptable salts and solvates thereof, (iii) beclomethasone dipropionate and physiologically acceptable solvates thereof, (iv) budesonide and physiologically acceptable solvates thereof, (v) triamcinolone acetonide and physiologically acceptable solvates thereof, (vi) iprawtopium bromide and physiologically acceptable salts and solvates thereof, and (vii) corticosteriod or bronchodilator.

Other examples of particle medicaments suitable for oral or nasal inhalation by means of the present aerosol composition include:

(viii) peptides, proteins, nucleic acids and derivatives thereof for use in the treatment and prevention of disease states, (ix) insulin, calcitonin, growth hormone, lutenising hormone release hormone (LHRH), leuprolide, oxytocin and physiologically acceptable salts and solvates thereof for use in the treatment and prevention of disease states including diabetes, and (x) any pharmacologically active particulate medicament having a median aerodynamic diameter within the range 0.05 to 11 μm administered in the form of an aerosol.

Further examples of appropriate medicaments may additionally be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, pbenylephrine, phenylpropanolamine, pirbuterol, reproterol, rimiterol, terbutaline, isoetharine, tulobuterol, or (−)4-amino-3,5-dichlor-α[[[6-[2-(2-pyridinyl)ethoxy] hexyl]methyl] benzenemethanol; diuretics, e.g., amiloride; anticholinergies, e.g., ipratropium, iotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol salineterol, fluticasone propionate and beclometasone dippropionate and salts or sovates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

The dosage requirements for any one medicament will be those conventionally employed in inhalers. For example where the first particulate material is salbutamol for use in relation to asthma the inhaler is employed as required, usually 1 or 2 actuations (i.e. puffs) between 0 and 4 times per day, with a single metered dose comprising 100 micrograms of salbutamol in a volume of metered liquid propellant between 20 and 150 µl.

The propellant is preferably selected from chlorofluorocarbons, from hydrofluorocarbons and from mixtures thereof. When the propellant is a chlorofluorocarbon such as CFC-11, CFC-12, CFC-114 the present invention can provide a suspension that obviates the need for the addition of unpalatable, or possibly even mildly toxic, surfactant. Alternatively the propellant can comprise hydrofluoroalkane such as 1,1,1,2-tetrafluoroethane (HFA-134a), 1,1,1,2,3,3,3-heptafluoropropane (HFA-227) and mixtures thereof. The combination of the first particulate material with the second particulate material both reduces the risk of the first particulate material aggregating undesirably and enhances the dispersement of the particulate medicament in the propellant. In manufacturing individual units of the suspension the increased dispersibility provided by the present invention obviates the need to prepare an initial bulk suspension by a homogenisation step. The combination of the first particulate material and the second particulate material can be readily wetted by and dispersed in HFA propellants in the absence of surfactant or added co-solvent. The suitable dispersion characteristics in HFA displayed by the presently provided combination of particulate materials permits its initial dispersion and any redispersion required following sedimenting or creaming with a small energy input, e.g. hand held shaking.

The present suspension can optionally contain any additional appropriate ingredients, for example pharmacologically acceptable excipients such as a surfactant, flavouring, buffer and preservatives in conventional acceptable amounts.

Embodiments of the present invention will now be described by way of example only with reference to the following Examples and the accompanying figures wherein:

FIG. 1 is a vertical cross section of a metered dose inhaler;

FIG. 2 is a vertical cross sectional view of the spring mechanism of the metered dose inhaler of FIG. 1;

FIG. 3 is a diagram showing the shot weights during the lifetime of three meter dosed inhalers;

FIG. 4 is a diagram showing shot potency over the lifetime of a metered dosed inhaler; and FIG. 5 is a diagram showing aerosol performance over the lifetime of a metered dose inhaler.

The present embodiments relate to an aerosol composition in the form of an inhaler.

COMPARATIVE EXAMPLES A TO T

Examples A to Q are comparative examples and demonstrate the suspension properties of a variety of particulate materials in the absence of a medicament.

Each suspension was assessed visually for its ease of dispersion on hand held shaking, its extent of aggregation and the quality of the suspension.

Ease of dispersion was scored on a scale of good (g), medium (m) and poor (p).

The extent of aggregation was scored on a scale of low, medium and high. Additionally the type of aggregation, if present, was recorded.

The quality of the suspension was scored on a scale of poor (p), poor-fair (p/f), fair (f), fair-good (f/g) and good (g).

Table I below gives the suspension properties of two types of lactose across a range of particle size. Example A employed a sample of a commercially available α-lactose monohydrate, "Lactochem (RTM) Regular for Inhalation" ex. Borculo of Chester, England. The particle size fractions of Examples B to G were achieved by sieving the commercially available lactose powder employed in Example A. Example H employed a commercially available αm-lactose monohydrate "Lactochem (RTM) Microfine for Inhalation". The particle size fractions employed in Examples I to M were achieved by sieving a commercially available lactose powder known as "Super-Tab" ex. Lactose New Zealand.

The sieved diameters were taken to be substantially equivalent to the volume diameter. The median particle diameter of the fraction employed in Example G comprising <38 $\mu$m particles of lactose was approximately 17 to 18 $\mu$m. The fraction employed in Example H comprising <10 $\mu$m particles of lactose had a median particle diameter of about 2.5 to 3.0 $\mu$m.

Each example comprised a suspension of 0.83 w/w % of lactose powder and 99.17 ww % of HFA-134a, which is 1,1,1,2-tetrafluoroethane.

TABLE I

| Example | Particulate Material | Size of Particle (μm) | Eau of Dispersion | Extent of Aggregation | Suspension Quality |
|---|---|---|---|---|---|
| A | lactose | 4–400 | g | low | f/g |
| B | lactose | >125 | g | low | f |
| C | lactose | 125–90 | g | low | f/g |
| D | lactose | 90–63 | g | low | f/g |
| E | lactose | 63–45 | g | medium-flocculation | f |
| F | lactose | 45–38 | g | high flocculation | p/f |
| G | lactose | <38 | g | high-flocculation | p/f |
| H | lactose | <10 | p/f | high-flocculation and irreversible aggregation | p |
| I | lactose - spray dried | >125 | g | Low | p/f |
| J | lactose - spray dried | 125–90 | g | Low | f |
| K | lactose - spray dried | 90–63 | g | low/medium-flocculation | f/g |
| L | lactose - spray dried | 63–45 | g | medium/high-flocculation | p/f |
| M | lactose - spray dried | <45 | g | high-flocculation | p/f |

As can be seen from the results in Table I each type of lactose displayed good dispersion properties, apart from Example H, and at larger particle sizes low aggregation and at smaller particle sizes a varying degree of flocculation. The suspension quality varied across the size range of particulate lactose peaking for each type at mid-range sizes. Example H however exhibited aggregates which could not be dispersed by hand held shaking.

Table II below gives the suspension properties of two further particulate materials each of which has a particle size volume diameter in the range of 125 to 90 μm. The leucine employed was L-leucine ex. Sigma of Poole, England. The glucose was d-glucose anhydrous ex. Fisons of Loughborough, England. A suspension was formed with each particulate material with each of HFA-134a, which is 1,1,1,2-tetrafluoroethane, and HFA-227, which is 1,1,1,2,3,3,3heptafluoropropane, as propellant.

TABLE II

| Example | Particulate material (w/w%) | Propellant (w/w%) | Ease of Dispersion | Extent of aggregation | Suspension Quality |
|---|---|---|---|---|---|
| N | leucine (0.83) | HFA-134a (99.17) | g | medium-flocculated | g |
| O | leucine (0.71) | HFA-227 (99.29) | g | low/medium-flocculated | g |
| P | glucose (0.83) | HFA-134a (99.17) | g | medium-flocculated | f/g |
| Q | glucose (0.71) | HFA-227 (99.29) | g | medium-flocculated | f/g |

Leucine is less dense than either of the propellants employed and had a tendency to cream i.e. rise to the surface of the propellant. Glucose is more dense than either of the propellants employed and had a tendency to sediment. In all cases however flocculated and other separated particulate material could be formed into a suspension on hand held shaking.

Examples R, S and T are comparative examples and demonstrate the suspension properties of a variety of particulate medicaments in the propellant HFA-134a in the absence of any second particulate material. The suspension properties measured by visual inspection were ease of dispersion, extent of aggregation and suspension quality and were scored as for Examples A to Q.

The results and compositions employed are given in Table III below. The median particle size given for each particulate medicament is its median volume diameter, which in each case is deemed approximately equivalent to the median aerodynamic diameter.

TABLE III

| Example | Particulate medicament (w/w %) | Median size of particle (μm) | Ease of dispersion | Extent of aggregation | Suspension quality |
|---|---|---|---|---|---|
| R | Salbutamol (0.08) | 2.71 | poor | high | poor |
| S | Salbutamol sulphate (0.08) | 3.57 | poor | high | poor |
| T | Budesonide (0.17) | 1.83 | poor | high | poor |

Each of Examples R, S and T exhibited poor dispersion and poor suspension qualities. In each case the majority of the particulate medicament was present in about 20 aggregates, which could not be deaggregated by hand held shaking.

EXAMPLES 1 TO 22 EMBODYING THE PRESENT INVENTION

Figure 2:
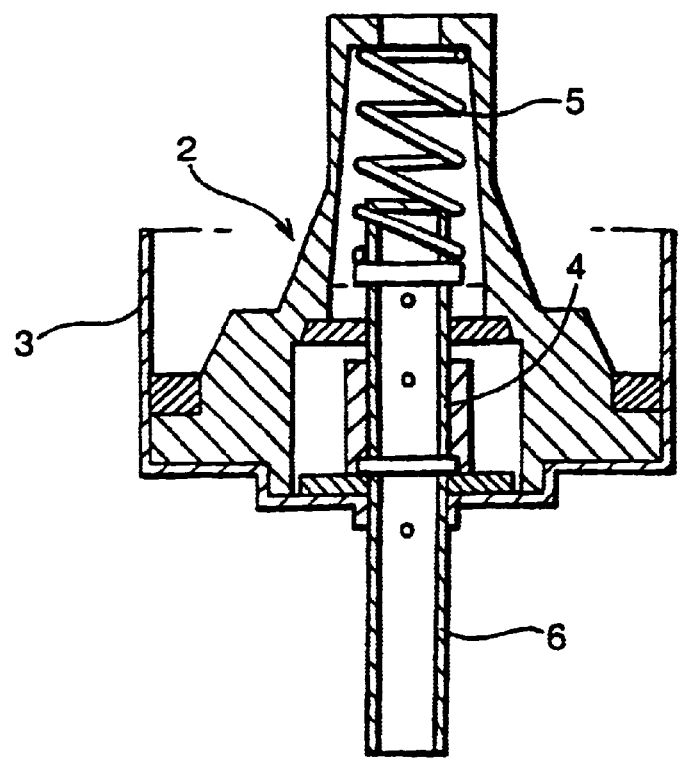

The metered dose inhaler shown in the accompanying FIGS. 1 and 2 in diagrammatic form comprises an inverted container (1) and a metering valve (2). The inverted container (1) is capable of withstanding a pressure up to $6.895 \times 10^5$ Pa (100 psig) and is closed by a closure cap (3). The metering valve (2) extends through the closure cap (3) and includes a fixed volume chamber (4), a spring mechanism (5) biased to maintain the valve closed when not being actuated and an outlet stem (6) which opens into an expansion chamber (7). The container (1) and metering valve (2) are mounted by support (8) in a holder (9) which is integral with an actuator tube (10) extending at an obtuse angle away from the holder (9). As can be seen in the drawing the expansion chamber (7) opens by way of a spray jet orifice (11) into the actuator tube (10). The container (1) contains the aerosol composition (12) comprising propellant and suspended particulate matter.

In use the container (1) is depressed relative to the holder (9) causing the chamber (4) to be open to the atmosphere and the fixed volume of liquefied gas therein to expand forcing the suspension into the expansion chamber (7) where the liquefied gas continues to expand and evaporate. The actuator tube (10) directs the aerosol so produced into the mouth or nose of the patient, as required for inhalation.

EXAMPLES 1 TO 7

Examples 1 to 7 demonstrate the suspension and aerosol properties for a range of compositions varying in the particulate medicament, the second particulate material having regard to both its particle size and its kind, and the propellant employed. The particulate size given in Table IV below for each of the medicaments is the mean volume diameter, which is deemed approximately equivalent to the mean aerodynamic diameter. The lactose particulate fractions employed were derived by sieving the commercially available product employed in Example A above, the sieved particle size were taken to be equivalent to the mean volume diameters. The leucine,and glucose particulate material employed were the same as those employed in Examples N and P above respectively, the particulate size given in Table IV below being the volume diameter.

In each of Examples 1 to 7 the particulate medicament is mixed together with the second particulate material by hand mixing in a mortar with a steel spatula at a ratio of particulate medicament to second particulate material of 1:10. The resulting mixture is dosed into the container of the metered dose inhaler described above, the closure cap crimped in place and the propellant added, as indicated in Table IV below. The balance of each composition comprised the 1:10 mixture of the particulate medicament and the second particulate material.

The resulting suspensions were assessed visually for ease of dispersion, suspension quality and extent of aggregation and scored as above, as set out under Examples A to R. The results are given in Table IV below.

Additionally, the shot weight and the aerosol characteristic of each suspension were assessed. The aerosol characteristics of each suspension were assessed using a 4 stage liquid impinger or Copley twin stage impinger operated at 60 L/min and the fine particle fraction, which provides an indication of the proportion of aerosol likely to reach a patient's lungs, recorded. A score of at least 40% was marked as good (g), 30–40% as fair (f) and less than 30% as poor (p).

The shot weight i.e. the weight of suspension metered with each actuation of the valve, was assessed. In each case the shot weight was found to be reproducible indicating no adverse clogging or blocking of the valve mechanism.

A above was employed as the second particulate material. In each of following Examples 15 to 19 commercially available lactose as employed in example A above was employed as the source of the lactose fractions used. The powder as received had a median volume diameter particle size of 80 $\mu$m. The range of volume diameter in the commercially available product was 4 to 400 $\mu$m.

The propellant employed in each of Examples 8 to 21 was HFA-134a which chemically is 1,1,1,2-tetrafluoroethane.

Examples 8 to 11 and Examples 13 and 20 contained salbutamol as a particulate medicament. The particulate salbutamol had a median volume diameter of 2.71 $\mu$m which is approximately equal to the median aerodynamic diameter for salbutamol.

Examples 12, 14 to 19 and 21 contained salbutamol sulphate as a particulate medicament. The particulate salbutamol sulphate had a median volume diameter of 3.57 $\mu$m, which in the case of salbutamol sulphate is approximately equal to the median aerodynamic diameter.

The particulate components of each of Examples 8 to 21 were dosed as indicated below and mixed together by hand mixing in a mortar with a steel spatula. The mixture was dosed as indicated below into a transparent container of a metered dose inhaler as described above, a metering valve crimped in place and the container filled with propellant as indicated below.

The suspensions so formed were assessed visually for ease of dispersion and suspension quality and each assessment was scored on a scale of poor (p), poor-fair (p/f), fair (f), fair-good (f/g), good (g).

The extent of aggregation of each suspension was also assessed visually and in each example was rated as low.

The shot weight i.e. the weight of suspension metered with each actuation of the valve, was assessed. In each case

TABLE IV

| Example | Particulate medicament ($\mu$m) | Second particulate material ($\mu$m) | Propellant (w/w %) | Ease of Dispersion | Extent of Aggregation | Suspension Quality | Fine particle fraction of aerosol |
|---|---|---|---|---|---|---|---|
| 1 | budesonide (1.83) | lactose (90-63) | HFA-134a (99.09) | g | low | f/g | f/g |
| 2 | salbutamol sulphate (3.57) | lactose (90-63) | HFA-227 (99.29) | g | low | f/g | g |
| 3 | salbutamol sulphate (3.57) | lactose (125-90) | HFA-227 (99.29) | g | low | f/g | g |
| 4 | salbutamol sulphate (3.57) | leucine (125-90) | HFA-113a (99.17) | g | medium-flocculated | f/g | g |
| 5 | salbutamol sulphate (3.57) | leucine (125-90) | HFA-227 (99.29) | g | medium-flocculated | f/g | g |
| 6 | salbutamol sulphate (3.57) | glucose (125-90) | HFA-134a (99.17) | g | low/medium-flocculated | f/g | g |
| 7 | salbutamol sulphate (3.57) | glucose (125-90) | HFA-227 (99.29) | g | medium-floculated | f/g | g |

For each of Examples 1 to 7 the scores given in Table IV indicate a composition having acceptable suspension and aerosol properties. The flocculated material in each of Examples 4 to 7 could be dispersed by hand held shaking.

EXAMPLES 8 TO 21

In each of the following Examples 8 to 14, 20 and 21 commercially available lactose powder as used in Example the shot weight was found to be reproducible indicating no adverse clogging or blocking of the valve mechanism.

The aerosol characteristics of each suspension of Examples 8 to 19 were assessed using a 4 stage liquid impinger or Copley twin stage impinger operated at 60 L/min and the fine particle fraction, which provides an indication of the proportion of aerosol likely to reach a patient's lungs, recorded. A score of at least 40% was marked as good (g), 30–40% as fair (f), and less than 30% as poor (p).

Examples 8 to 13 investigate the effect of the weight ratio of the particulate medicament to particulate lactose in the initial blend of particulate components by varying the ratio through the range 1:2.5 to 1:100. The overall composition in terms of the amount of propellant added was determined having regard to providing a therapeutic dose of medicament per actuation.

The compositions prepared and their attendant results in terms of ease of dispersion, suspension quality and fine particle fraction of aerosol are given in Table V below.

TABLE V

| Example | Blend (wt %) | Propellant (wt %) | Wt. Ratio medicament: lactose | Ease of dispersion | Extent of aggregation | Suspension quality | Fine particle fraction of aerosol |
|---|---|---|---|---|---|---|---|
| 8 | 0.29 | 99.71 | 1:2.5 | f | low | f/g | g |
| 9 | 0.91 | 99.09 | 1:10 | g | low | f/g | g |
| 10 | 2.15 | 97.85 | 1:25 | g | low | f/g | g |
| 11 | 4.21 | 95.79 | 1:50 | g | low | f/g | f/g |
| 12 | 6.77 | 93.33 | 1:67 | g | low | f/g | f/g |
| 13 | 8.35 | 91.65 | 1:100 | g | low | f/g | p/f |

As can be seen from Table V the ease of dispersion of the blend in the propellant increased as the proportion of particulate lactose to particulate medicament increased. At higher levels of particulate lactose to particulate medicament however the measurable fine particle fraction i.e. the particulate medicament of the aerosol decreased.

In the following Examples 14 to 19 the particle size of the particulate lactose was varied to determine its effect. Different size fractions of lactose were achieved by sieving the commercially available product, the sieved fractions were deemed to have particle diameter substantially equivalent to the volume diameter. The fraction employed in Example 15 comprising lactose particles <38 μm had a median particle size of approximately 17 to 18 μm. The mixture contained a weight ratio of particulate salbutamol sulphate to lactose of 1:10 and the mixture comprised in each instance 1.1 wt % of the total composition with the balance comprising 98.90% propellant to give on each actuation a therapeutic dose of medicament. The results in terms of case of dispersion, suspension quality and fine particle fraction of aerosol are given in Table VI below.

TABLE VI

| Example | Particle size of material (μm) | Extent of aggregation | Ease of dispersion | Suspension quality | Flue particle fraction of aerosol |
|---|---|---|---|---|---|
| 14 | 4–400 | low | g | f/g | g |
| 15 | <38 | low | g | g | — |
| 16 | 38–45 | low | g | g | f |
| 17 | 45–63 | low | g | g | f/g |
| 18 | 63–90 | low | g | f/g | f/g |
| 19 | 90–125 | low | g | f/g | f/g |

Each of Examples 14 to 19 produced a suspension with good ease of dispersion properties. The suspension qualities were acceptable in all cases although were superior in the <38, 38 to 45 and 45 to 63 μm ranges. The aerosol properties however in terms of fine particle fraction of medicament were better with particulate lactose of the greater particulate size.

In present Example 20 the fine particle fraction of aerosol tests were carried out on a metered dosed inhaler, as described above, containing the composition of Example 9 above to demonstrate the efficacy of the suspension throughout the life of an inhaler.

The results are given in Table VII below in terms of shot nos. i.e. the counted actuations of the valve throughout the inhaler's life.

TABLE VII

| Shot nos. | Fine particle fraction of aerosol |
|---|---|
| 4–5 | g |
| 41–42 | g |
| 62–63 | g |

In present Example 21 the composition of Example 12 above was centrifuged at 5000 g for 30 mins. The centrifuged suspension was observed to demonstrate a good ease of dispersion, a low extent of aggregation and a fair/good suspension quality. The test was designed to demonstrate the propensity or otherwise of the suspension to aggregate irreversibly or cake over time.

EXAMPLE 22

Example 22 employed ball milled L-Leucine as the second particulate material having a sieve fraction of 90 to 125 μm, and salbutamol sulphate as employed in Example S above. The weight ratio of L-Leucine to salbutamol sulphate was 10:1. The mixture was weighed directly into the canister, the valve crimped, and HFA-134a propellant added in a weight ratio of salbutamol sulphate/leucine: propellant of 1:10. The actuation dose was 100 μg. The unit was briefly hand shaken prior to each firing.

The canister was fired in a pattern designed to imitate the potential use of metered dose inhaler when used by a potential patient. The canister was therefore fired as two shots up to four times daily. Individual shot weights were measured. Aerosol performance and shot potency were determined at the beginning, middle and end of the life of the unit (i.e. on days 0,20 and 42), Aerosol performance was assessed by measuring fine particle fraction using a four stage liquid impinger.

Shot potency was determined on individual actuations.

Figure 3:
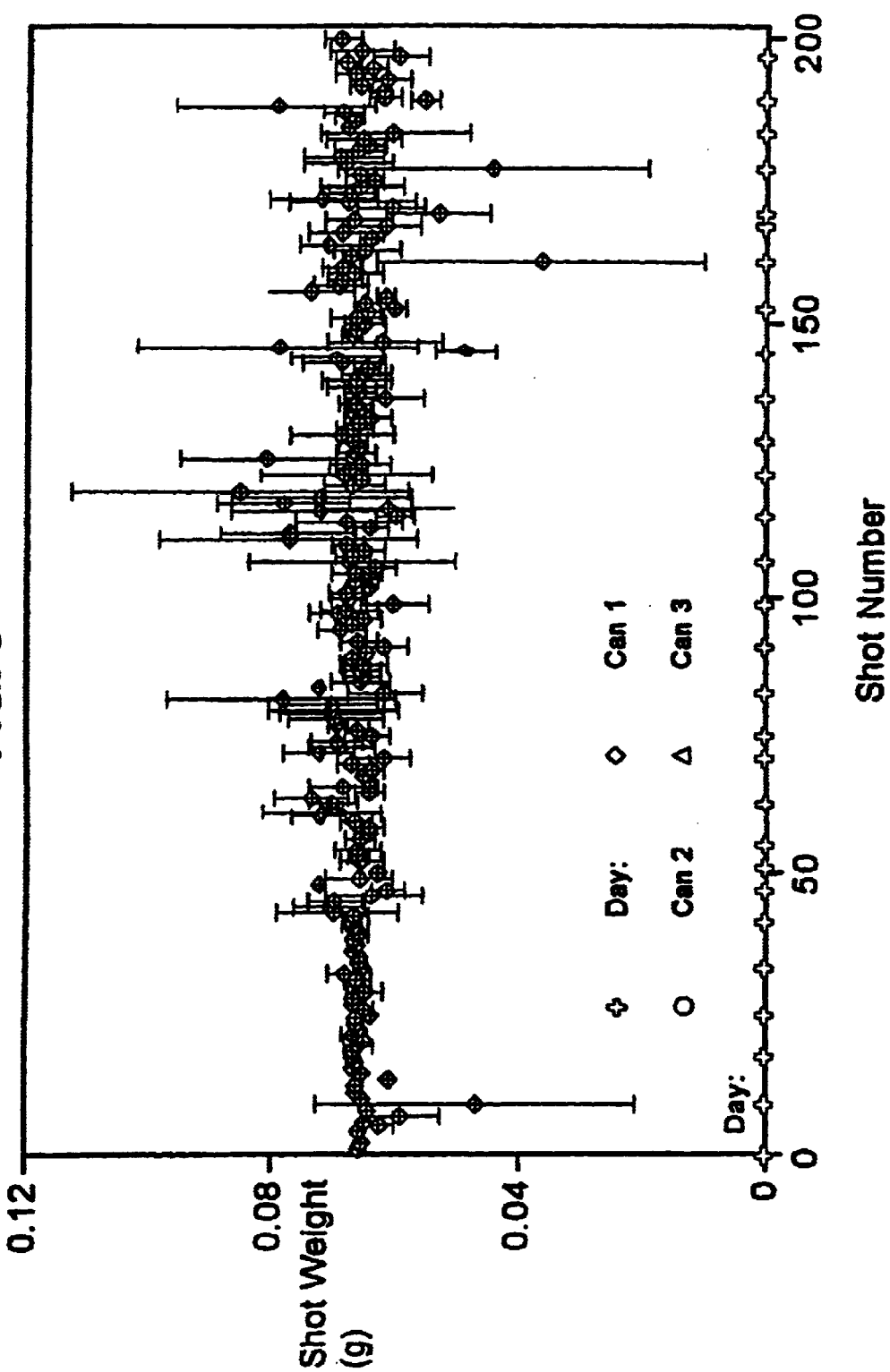

FIG. 3 shows the results of the mean shot weight versus shot number for the canister collected over 42 days, following nominal actuation timetable of two shots fired four times daily. The shot weights can be seen to be reasonably reproducible over the 42 days period and are thus an indicator of valve integrity. Few individual shots lie away the intended shot actuation weight. The variation in a patient actuated device is deemed acceptable.

Figure 4:
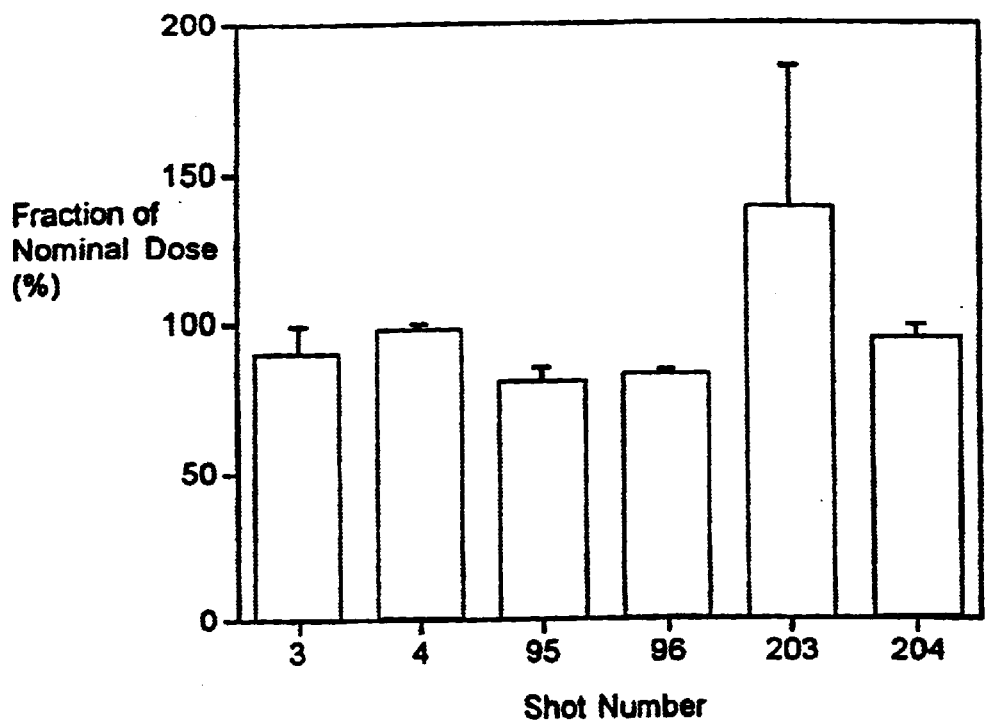

FIG. 4 shows in diagrammatic form the shot potency i.e. the drug dose per actuation at the start, middle and end of the lifetime testing shown in FIG. 3. The figure shows reproducible and high recovery of the nominal dose at the beginning, middle and end of the unit life, even after storage, when not being tested, at 40° C., 75% R.H. for 42 days. The increased potency of shot 203 is a consequence of a high shot weight. If the potency is normalised for shot weight it is comparable for the data for the other shots in FIG. 4. The data of FIG. 4 indicate that a homogeneous suspension is formed from which representative aliquots are measured.

Figure 5:
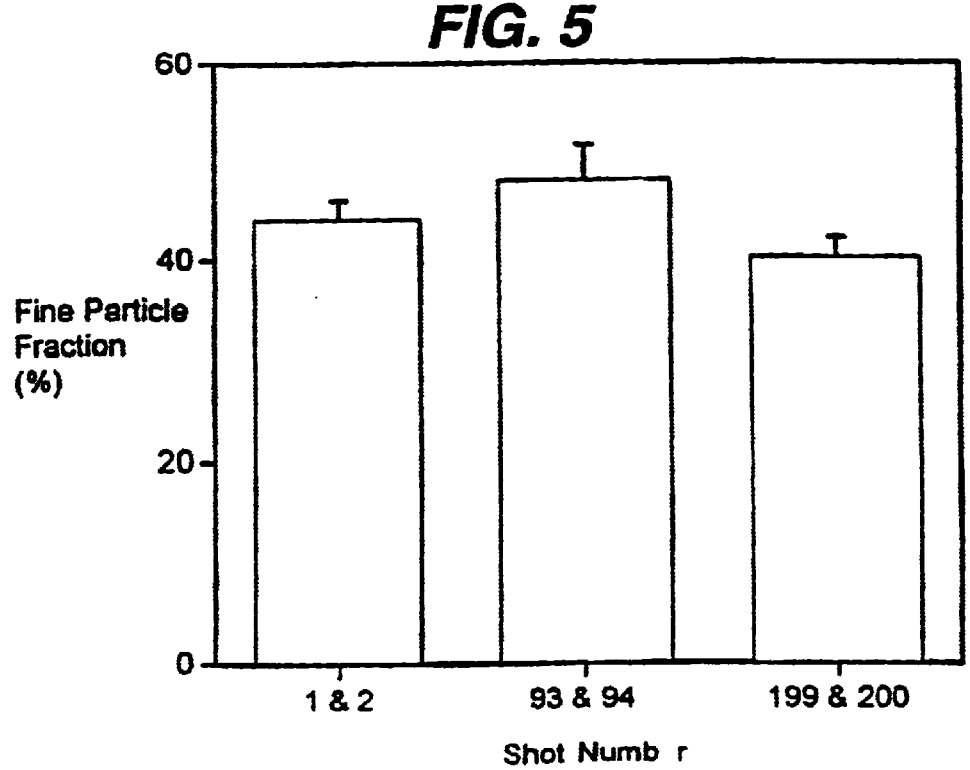

FIG. 5 shows that good aerosol performance was maintained throughout the life of the canister.

What is claimed is:

1. Aerosol composition comprising a propellant and contained therein a first particulate material comprising particles having a median aerodynamic diameter within the range 0.05 $\mu$m to 11 $\mu$m and a second particulate material comprising particles having a median volume diameter within the range 15 to 200 $\mu$m, wherein the first and second particulate materials are segregated upon aerosolization into a respirable first fraction and a non-respirable second fraction.

2. Composition according to claim 1 wherein the second particulate material has a median volume diameter within the range 20 to 125 $\mu$m.

3. Composition according to claim 1 wherein the weight ratio of first particulate material to second particulate material in the composition lies in the range 1:0.1 to 1:500.

4. Composition according to claim 3 wherein the weight ratio of first particulate material to second particulate material in the composition lies in the range 1:10 to 1:100.

5. Composition according to claim 1 wherein the first particulate material has a median aerodynamic diameter within the range 1 to 10 $\mu$m.

6. Composition according to claim 1 wherein the second particulate material has a Mohs hardness value of less than 5.

7. Composition according to claim 1 wherein the second particulate material has a Carr Index value:
for particles more than 100 um in size of less than 14%;
for particles 40 to 100 um in size of less than 28%;
for particles 20 to 40 um in size of less than 35%; and
for particles less than 20 um in size of less than 65%.

8. Composition according to claim 1 wherein the solubility of the first particulate material in the propellant is less than 49.9 wt % with respect to the total weight of the substance present in the composition comprising the first particulate material.

9. Composition according to claim 1 wherein the solubility of the second particulate material in the propellant is less than 49.9 wt % with respect to the total weight of the substance present in the composition comprising the second particulate material.

10. Composition according to claim 1 wherein the composition comprises at least 80 wt % and up to 99.999 wt % propellant.

11. Composition according to claim 10 wherein the total of the first and second particulate material comprises at least 0.001 wt % and up to 20 wt % of the composition.

12. Composition according to claim 1 further comprising a surfactant, flavouring material, buffer, preservative or any mixture thereof.

13. Composition according to claim 1 wherein the propellant is selected from the group consisting of chlorofluorocarbons, hydrofluorocarbons, and mixtures thereof.

14. Composition according to claim 13 wherein the propellant is selected from the group consisting of hydrofluorocarbons and mixtures thereof.

15. Composition according to claim 14 wherein the propellant is a hydrofluoroalkane selected from the group consisting of 1,1,1,2-tetrafluoroethane, 1,1,1,2,3,3,3-heptafluoropropane, and mixtures thereof.

16. Composition according to claim 1 wherein the first particulate material is a medicament.

17. Composition according to claim 16 wherein the medicament is selected from the group consisting of salbutamol, salbutamol sulphate, terbutaline, terbutaline sulphate, ipratropium bromide or any physiologically acceptable salts or solvates thereof; beclomethasone diprionate, budesonide, triamcinolone acetonide or any physiologically acceptable solvates thereof; corticosteroid, bronchodilator; peptides, proteins, nucleic acids or derivatives thereof; insulin, calcitonin, growth hormone, lutensing hormone releasing hormone, leuprolide, and oxytocin or any physiologically acceptable salts or solvates thereof, and any mixture thereof.

18. Composition according to claim 17 wherein the medicament is salbutamol sulphate.

19. Composition according to claim 16 wherein the medicament is salmeterol xinafoate or a mixture of salmeterol xinafoate with any one of the group consisting of salbutamol, salbutamol sulphate, terbutaline, terbutaline sulphate, ipratropium bromide or any physiologically acceptable salts or solvates thereof; beclomethasone diprionate, budesonide, triamcinolone acetonide or any physiologically acceptable solvates thereof; corticosteroid, bronchodilator; peptides, proteins, nucleic acids or derivatives thereof; insulin, calcitonin, growth hormone, lutensing hormone releasing hormone, leuprolide, and oxytocin or any physiologically acceptable salts or solvates thereof, and any mixture thereof.

20. Composition according to claim 16 wherein the medicament is fluticasone propionate or a mixture of fluticasone propionate with any one of the group consisting of salbutamol, salbutamol sulphate, terbutaline, terbutaline sulphate, ipratropium bromide or any physiologically acceptable salts or solvates thereof; beclomethasone diprionate, budesonide, triamcinolone acetonide or any physiologically acceptable solvates thereof; corticosteroid, bronchodilator, peptides, proteins, nucleic acids or derivatives thereof; insulin, calcitonin, growth hormone, lutensing hormone releasing hormone, leuprolide, and oxytocin or any physiologically acceptable salts or solvates thereof, and any mixture thereof.

21. Composition according to claim 16 wherein the medicament is beclomethasone dipropionate or a physiologically acceptable solvate thereof, or any mixture thereof with any one of the group consisting of salbutamol, salbutamol sulphate, terbutaline, terbutaline sulphate, ipratropium bromide or any physiologically acceptable salts or solvates thereof; beclomethasone diprionate, budesonide, triamcinolone acetonide or any physiologically acceptable solvates thereof; corticosteroid, bronchodilator; peptides, proteins, nucleic acids or derivatives thereof; insulin, calcitonin, growth hormone, lutensing hormone releasing hormone, leuprolide, and oxytocin or any physiologically acceptable salts or solvates thereof, and any mixture thereof.

22. Composition of claim 1 wherein the second particulate material is selected from the group consisting of amino acids, di-, tri-, oligo-, and poly-peptides, proteins, physiologically acceptable derivatives, forms, salts, and solvates thereof, and mixtures thereof.

23. Pharmaceutical composition comprising a propellant and contained therein a particulate medicament comprising particles having a median aerodynamic diameter within the range 0.05 to 11 μm and a second particulate material comprising particles having a median volume diameter within the range 15 to 200 μm, wherein the second particulate material is selected from the group consisting of amino acids, di-, tri-, oligo-, and poly-peptides, proteins, physiologically acceptable derivatives, forms, salts, and solvates thereof, and mixtures thereof, and wherein the particulate medicament and second particulate materials are segregated upon aerosolization into a respirable first fraction and a non-respirable second fraction.

24. A method for preparing an aerosol composition according to any one of claims 1 to 23 comprising:
   (a) forming a mixture of the first particulate material and the second particulate material;
   (b) dispensing measured portions of respectively the said mixture and the propellant into a container; and
   (c) sealing the container.

25. The method according to claim 24 wherein the mixture is dispensed into the container before the propellant.

26. A method for preparing a composition according to any one of claims 1 to 23 comprising admixing the ingredients together prior to dispensing into a container and sealing the container.

27. The method according to claim 26 wherein the container includes an outlet valve.

28. A method of administering a particulate medicament to a patient in need thereof comprising forming an aerosol from the aerosol composition according to any one of claims 18 to 23 and the patient inhaling the aerosol.

29. An aerosol composition according to any one of claims 18 to 23 for use in the treatment of respiratory disorders.

30. A container containing a composition according to any one of the preceding claims wherein the container includes a valve outlet.

31. A container according to claim 30 wherein the valve outlet is a metered dose valve.

32. A container according to claim 31 in the form of a metered dose inhaler.

33. An inhalation device incorporating a container according to claim 30.

34. A mixture of first particulate material having a median aerodynamic diameter within the range 0.05 to 11 μm and a second particulate material having a median volume diameter within the range of 15 to 200 μm, wherein the second particulate material is selected from the group consisting of amino acids, di-, tri-, oligo-, and poly-peptides, proteins, physiologically acceptable derivatives, forms, salts, and solvates thereof, and mixtures thereof, and wherein the first and second particulate materials are segregated upon aerosolization into a respirable first fraction and a non-respirable second fraction.

35. Aerosol composition comprising a propellant and contained therein a first particulate material comprising particles having a median aerodynamic diameter within the range 0.05 μm to 11 μm and a second particulate material comprising particles having a median volume diameter within the range 38 to 200 μm.

36. Composition of claim 35, wherein the second particulate material is a carbohydrate.

37. Composition of claim 36, wherein the carbohydrate is selected from the group consisting of sugars, mono-, di-, tri-, oligo-, and poly-saccharides, and any physiologically acceptable derivatives, salts, forms, and solvates thereof, and any mixtures thereof.

38. Composition of claim 35, wherein the second particulate material has a median volume diameter within the range 38 to 63 μm.

39. Composition of claim 38, wherein the second particulate material has a median volume diameter within the range 45 to 63 μm.

40. Pharmaceutical composition comprising a propellant and contained therein a particulate medicament comprising particles having a median aerodynamic diameter within the range 0.05 to 11 μm and a second particulate material comprising particles having a median volume diameter within the range 38 to 200 μm.

41. Composition of claim 40, wherein the second particulate material is a carbohydrate.

42. Composition of claim 41, wherein the carbohydrate is selected from the group consisting of sugars, mono-, di-, tri-, oligo-, and poly-saccharides, and any physiologically acceptable derivatives, salts, forms, and solvates thereof, and any mixtures thereof.

43. Composition of claim 40, wherein the second particulate material has a median volume diameter within the range 38 to 63 μm.

44. Composition of claim 43, wherein the second particulate material has a median volume diameter within the range 45 to 63 μm.

45. Composition of claim 40, wherein the first and second particulate materials are segregated upon aerosolization into a respirable first fraction and a non-respirable second fraction.

46. A mixture of first particulate material having a median aerodynamic diameter within the range 0.05 to 11 μm and a second particulate material having a median volume diameter within the range of 38 to 200 μm.

47. Mixture of claim 46, wherein the second particulate material is a carbohydrate.

48. Mixture of claim 47, wherein the carbohydrate is selected from the group consisting of sugars, mono-, di-, tri-, oligo-, and poly-saccharides, and any physiologically acceptable derivatives, salts, forms, and solvates thereof, and any mixtures thereof.

49. Mixture of claim 46, wherein the second particulate material has a median volume diameter within the range 38 to 63 μm.

50. Mixture of claim 49, wherein the second particulate material has a median volume diameter within the range 45 to 63 μm.

51. Mixture of claim 46, wherein the first and second particulate materials are segregated upon aerosolization into a respirable first fraction and a non-respirable second fraction.

* * * * *